(12) United States Patent
Schmidt

(10) Patent No.: US 8,375,833 B2
(45) Date of Patent: Feb. 19, 2013

(54) EXACT WEIGHT CUTTING SYSTEM FOR FOOD PRODUCTS

(75) Inventor: Richard J. Schmidt, Fond du Lac, WI (US)

(73) Assignee: Marchant Schmidt, Inc., Fond du Lac, WI (US)

( * ) Notice: Subject to any disclaimer, the term of this patent is extended or adjusted under 35 U.S.C. 154(b) by 0 days.

(21) Appl. No.: 13/547,576

(22) Filed: Jul. 12, 2012

(65) Prior Publication Data

US 2012/0272803 A1    Nov. 1, 2012

Related U.S. Application Data

(62) Division of application No. 12/696,386, filed on Jan. 29, 2010, now Pat. No. 8,276,490.

(51) Int. Cl.
| B26D 7/00 | (2006.01) |
| B26D 1/46 | (2006.01) |
| A47J 43/00 | (2006.01) |
| H04N 7/18 | (2006.01) |

(52) U.S. Cl. .................. 83/77; 83/803; 99/537; 378/54; 378/58; 348/86

(58) Field of Classification Search .............. 83/77, 176, 83/19, 75.5, 522.26, 620, 356, 762, 932, 83/17, 522.11, 624, 631, 76.1, 76.7, 761, 83/454, 466.1, 86, 102, 803; 99/537; 378/54; 378/58; 348/86
See application file for complete search history.

(56) References Cited

U.S. PATENT DOCUMENTS

| 1,931,982 | A |  | 4/1931 | Faillers |
| 3,200,864 | A |  | 8/1965 | Gillman |
| 3,204,676 | A |  | 9/1965 | Gillman |
| 3,510,944 | A |  | 5/1970 | Johanski, Jr. |
| 3,519,051 | A |  | 7/1970 | Badgley et al. |
| 3,636,630 | A |  | 1/1972 | Budahn |
| 4,208,931 | A |  | 6/1980 | Collins |
| 4,318,321 | A |  | 3/1982 | De Mattos |
| 4,608,896 | A |  | 9/1986 | Topp |
| 4,646,602 | A |  | 3/1987 | Bleick |
| 4,875,254 | A | * | 10/1989 | Rudy et al. ..................... 452/157 |
| 4,991,477 | A |  | 2/1991 | Butt et al. |
| 5,784,937 | A |  | 7/1998 | Wygal et al. |
| 5,937,080 | A |  | 8/1999 | Vogeley et al. |

(Continued)

FOREIGN PATENT DOCUMENTS

| DE | 4218267 | 12/1993 |
| DE | 19820058 | 12/1999 |

(Continued)

*Primary Examiner* — Ghassem Alie

(74) *Attorney, Agent, or Firm* — Reinhart Boerner Van Deuren s.c.

(57) ABSTRACT

A system for cutting blocks of food product into bars of substantially equal weight. The system includes a cutter conveyor configured to receive incoming blocks of food product and move the blocks along an in-line processing path in a plane for cutting; a programmable logic controller coupled to the cutter conveyor; and, multiple stations associated with the cutter conveyor. One such station is a camera vision system configured to create an image of the slab portion, and further including a camera controller coupled to the vision system and the PLC, and configured to determine an optimized cut solution of the slab portion from the image and data related to the food product, and is configured to provide the cut solution to the PLC. The PLC is configured to control the cutting of the food product, based on the optimized cut solution, into bars of substantially equal weight.

15 Claims, 4 Drawing Sheets

U.S. PATENT DOCUMENTS

| | | |
|---|---|---|
| 6,032,561 A | 3/2000 | Lonn et al. |
| 6,101,913 A | 8/2000 | Gahmberg et al. |
| 6,164,174 A | 12/2000 | Sigurdsson et al. |
| 6,468,570 B1 | 10/2002 | Haddad et al. |
| 6,487,949 B1 | 12/2002 | Dharia |
| 6,549,823 B1 | 4/2003 | Hicks et al. |
| 6,655,248 B1 | 12/2003 | Johnson |
| 7,044,846 B2 | 5/2006 | Eilertsen |
| 7,055,419 B2 | 6/2006 | Sandberg |
| 7,540,221 B1 | 6/2009 | Schmidt |
| 7,623,249 B2 | 11/2009 | Sandberg et al. |
| 2009/0223387 A1* | 9/2009 | Schmidt .......................... 99/537 |

FOREIGN PATENT DOCUMENTS

| | | |
|---|---|---|
| EP | 500478 | 2/1991 |

* cited by examiner

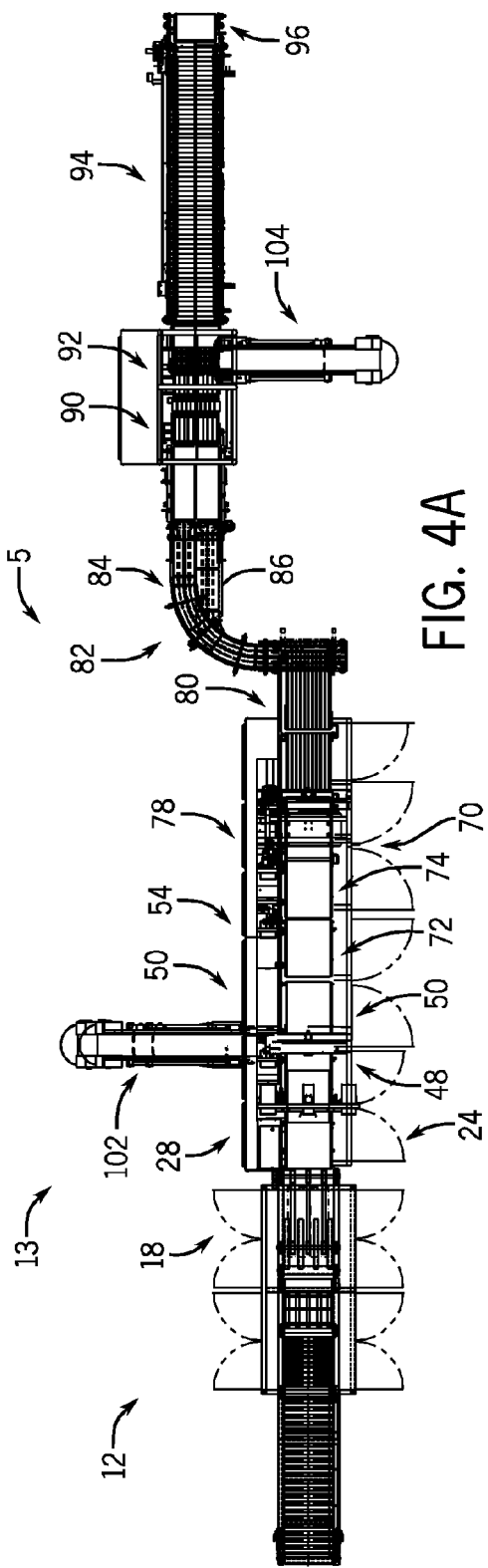
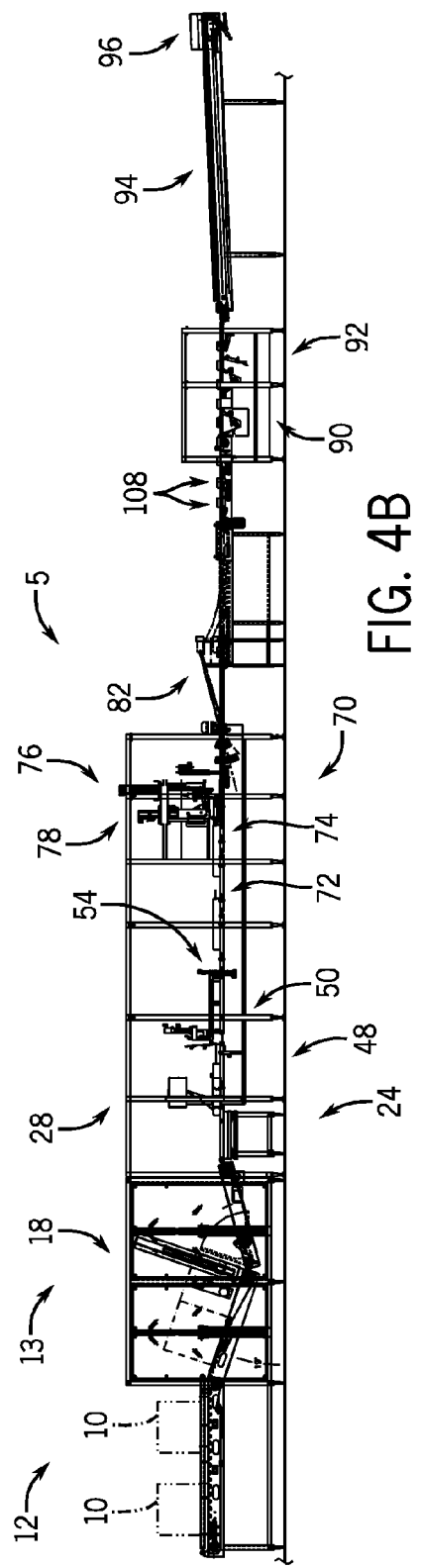
FIG. 4A
FIG. 4B

EXACT WEIGHT CUTTING SYSTEM FOR FOOD PRODUCTS

CROSS-REFERENCE TO RELATED APPLICATION

This patent application is a divisional application of U.S. patent application Ser. No. 12/696,386, filed Jan. 29, 2010, now U.S. Pat. No. 8,276,490, issued Oct. 2, 2012 with the title "Exact Weight Cutting System for Food Products," the entire teachings and disclosure of such application is incorporated herein by this reference.

BACKGROUND

Field of the Invention

The present invention relates generally to food processing, and more particularly to a conveyor system including a camera vision system configured to optimize a cut solution to maximize the output of a food product from a bulk size block to exact weight individual bars.

Many food products, such as cheese, are produced in block form and a multi-stage cutting operation is used for cutting the blocks into smaller portions for retail sale. In conventional systems of cutting large blocks of cheese, or other food products, the cheese is cut into a plurality of strips and then cut into small pieces. Such conventional systems produce as much as 15% of waste, i.e. not suitable for retail sale, and also result in giveaway of product of as much as 1% over a target weight of acceptable retail product. The system disclosed herein maximizes the yield from a specific slab of food product to result in less than 10% of waste and not more than ½% of giveaway over a specific target weight of food product, resulting in the maximum number of individual bars of food product of substantially equal weight from the original block of food product.

The apparatus of the present disclosure must be of construction which is both durable and long lasting, and it should also require little or no maintenance to be provided by the user throughout its operating lifetime. In order to enhance the market appeal of the apparatus of the present disclosure, it should also be of inexpensive construction to thereby afford it the broadest possible market. Finally, it is also an objective that all of the aforesaid advantages and objectives be achieved without incurring any substantial relative disadvantage.

SUMMARY

The disadvantages and limitations of the background art discussed above are overcome by the present disclosure.

There is disclosed a system for cutting blocks of food product into individual bars of substantially equal weight. The system includes a cutter conveyor configured to receive incoming blocks of food product and move the blocks along a continuum, in-line processing path for cutting; a programmable logic controller coupled to the cutter conveyor; and, a plurality of stations associated with the cutter conveyor with each station coupled to the programmable logic controller. The plurality stations includes a) a slab cutter station configured to cut a slab portion from a block of food product; b) a weight station configured to weigh the slab portion; c) camera vision system configured to create a 3D image of the slab portion, the camera vision system including a camera controller coupled to the camera vision system and to the programmable logic controller, the camera vision system being configured to determine an optimized cut solution of the slab portion from the 3D image and from select data characterizing the food product being cut, the camera vision system being configured to provide the cut solution to the programmable logic controller; d) a trim cutter station configured to square the leading edge of the slab portion; e) a slit cutter station configured to cut the slab portion into a plurality of elongated bars of substantially equal weight; f) an index station configured to position the plurality of bars; and g) a width portion cutter station configured to simultaneously, traversely cut the plurality of elongated bars into individual bars of substantially equal weight. The programmable logic controller is configured to control the cutting of the food product, based on the optimized cut solution, into individual bars of substantially equal weight.

There is further provided a system for cutting blocks of food product into individual bars of substantially equal weight. The system includes a conveyor system configured with a plurality of stations, with a station each to cut a slab portion of the food product, weigh the slab portion, trim the slab portion, cut the slab portion into a plurality of elongated bars, cut simultaneously the plurality of elongated bars into individual bars of substantially equal weight, weigh the individual bars and discard any individual bar that is either over or under a specified weight. A three camera vision system is coupled to the conveyor system. The vision system included a camera controller configured to image the slab portion and determine an optimal cut solution based on the image and from select data related to the slab portion of food product. A programmable logic controller is coupled to the conveyor system and configured to control each of the stations, the programmable logic controller is also coupled to the vision system and configured to optimize, based on the cut solution, the cuts to the slab portion to produce the individual bars of substantially equal weight and maximize total yield of individual bars from the slab portion and minimize the give-away for the food product.

There is also provided a system for cutting blocks of food product into individual bars of substantially equal weight. The system includes a cutter conveyor configured to receive incoming blocks of food product and move the blocks along a continuum, in-line processing path for cutting; a programmable logic controller coupled to the cutter conveyor; and, a plurality of stations associated with the cutter conveyor with each station coupled to the programmable logic controller. The plurality of stations includes a) a slab cutter station configured to cut a slab portion from a block of food product; b) a weight station configured to weigh the slab portion; c) a camera vision system configured to create a 3D image of the slab portion, the camera vision system including a camera controller coupled to the camera vision system and the programmable logic controller, the camera vision system being configured to determine an optimized cut solution of the slab portion from the 3D image and from select data related to the food product being cut, the camera vision system being configured to provide the cut solution to the programmable logic controller; d) a trim cutter station configured to square the leading edge of the slab portion; e) a slit cutter station configured to cut the slab portion into a plurality of elongated bars of substantially equal weight; f) an index station configured to align the plurality of bars; and g) a width portion cutter station configured to simultaneously, traversely cut the plurality of elongated bars simultaneously into individual bars of substantially equal weight; a transport conveyor coupled to the cutter conveyor, the transport conveyor configured to reorientate the individual bars 90 degrees and separate each individual bar, the transport conveyor including an upper tier and a lower tier with each tier configured to receive and move the individual bars; a weight belt conveyor, coupled to the transport conveyor, configured to weigh each individual bar and reject any individual bar that is either over or under a specified weight as determined by the programmable logic controller; and an accumulation conveyor coupled to the weight belt conveyor and configured to move the individual bars of substantially equal weight to a packaging station.

The apparatus of the present disclosure is of a construction which is both durable and long lasting, and which will require little or no maintenance to be provided by the user throughout its operating lifetime. The apparatus of the present disclosure is also of inexpensive construction to enhance its market appeal and to thereby afford it the broadest possible market. Finally, all of the aforesaid advantages and objectives are achieved without incurring any substantial relative disadvantage.

DESCRIPTION OF THE DRAWINGS

These and other advantages of the present disclosure are best understood with reference to the drawings, in which:

FIG. 4A is a top plan view of the cutter conveyor of an exemplary embodiment of the system for cutting blocks of food product illustrated in FIG. 1

FIG. 4B is a side elevation plan view of the system illustrated in FIG. 4A.

DETAILED DESCRIPTION OF THE EXEMPLARY EMBODIMENTS

Cheese typically is produced in large blocks, cheese milk curd and other ingredients are poured into a bag lined mould, resulting in irregular surface features and rounded corners. The top surface of the block is typically formed by pressing plywood panel down onto the cheese curd in the box (mould) using springs. The springs are not equally tensioned which results in the block surface being uneven, sloped and irregular. This results in the leading edge of each bar cut from the block to have an irregular sloped leading face when presented to the food product optimizing process described herein.

Each bar of food product is weighed and dimensionally scanned to determine the bar density. The bar density may be assumed to be uniform or non-uniform. In the uniform case the total measured bar weight is divided by the total volume. In the non-uniform case a number of zones may be defined in which the density is assumed to be more or less than the average bar density. The definition and selection of the density zones is done with an interface of the optimizer camera vision system 28 controller.

Based on target product weights the system determines the cut locations for each defect free piece and communicates the cutting decision to the process control system for example a programmable logic controller 14 (PLC), for positioning and cutting with ultrasonic cutting knives and wire cutters.

Figure 1:
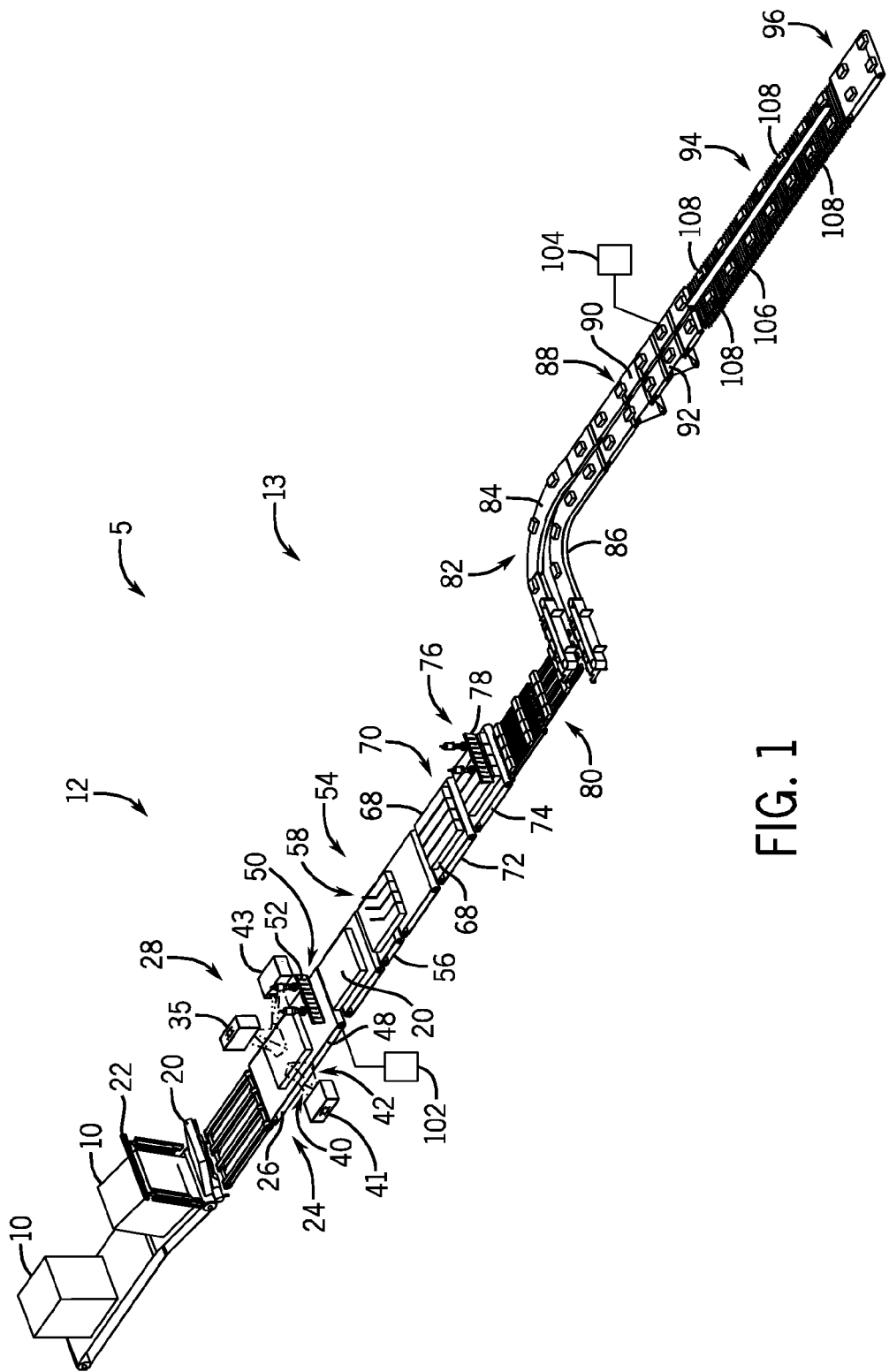
FIG. 1 is a schematic, perspective illustration of an exemplary embodiment a system for cutting blocks of a food product into individual bars of substantially equal weight.

An exemplary embodiment of a system for cutting blocks of a food product 5, for example cheese, into individual bars of substantially equal weight includes a plurality of conveyor belt segments coupled together as illustrated in FIG. 1 and functioning as described below. The conveyor belt segments comprising the plurality of stations 13 of the system 5 includes: weight station 24, camera vision system 28, trim cutter station 50, slit cutter station 54, staging and index station 70, width option cutter station 76, and packaging station 96.

Figure 3:
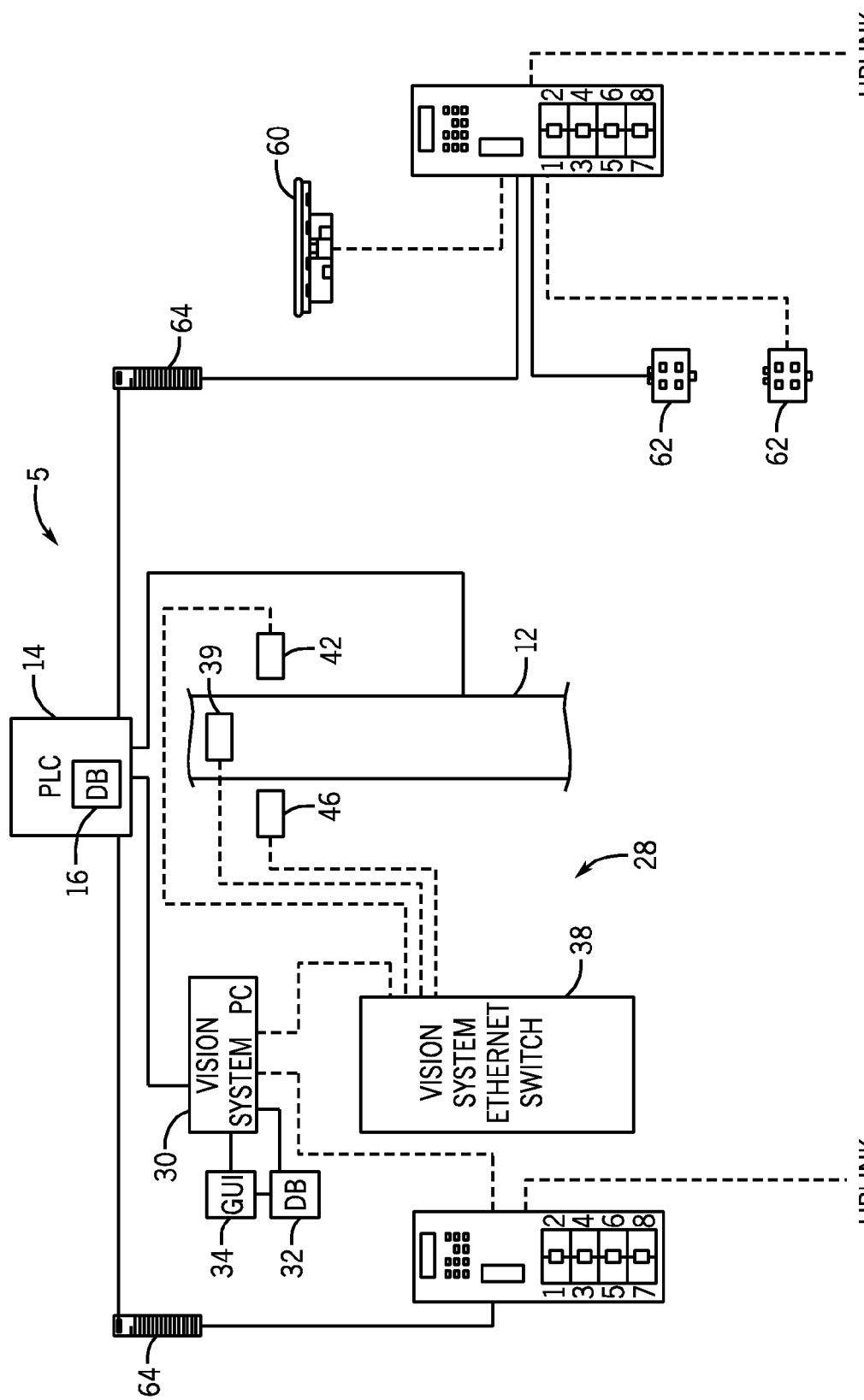
FIG. 3 is a schematic block diagram of an exemplary embodiment of a control scheme of the system illustrated in FIG. 1.

Referring to FIG. 3, a programmable logic controller (PLC) 14 on a microprocessor, or other sustainable control device, controls the function and operation of the system for cutting blocks of food product 5 described herein. The PLC 14 functions in cooperation with the camera vision system controller 30, which for example can be an industrial type computer, personal computer or other suitable control device. As described below, the camera vision system 28 determines an optimized cut solution for each slab portion 20 cut from the block of food product 10.

The optimized cut solution maximizes the number of individual bars of food product 108 having substantially equal weight and minimizes the amount of giveaway (amount of food product over the target weight) for a specific slab portion 20 of food product. Conventional food cutting systems typically obtain 85-88% yield of suitable individual bars from a slab portion (the remaining 12-15% of food product is otherwise further processed or discarded) with 1% of giveaway. The system 5 disclosed herein yields 90-95% of suitable individual bars of substantially equal weight with less than ½% of giveaway.

The PLC 14 synchronizes the several operations of the plurality of stations 13 comprising the system 5. The PLC 14 controls and exchanges data with the several servomotors (not shown), sensors (not shown), and the conveyor belts in accord with the optimized cut solution determined by the camera vision system 28.

Figure 2:
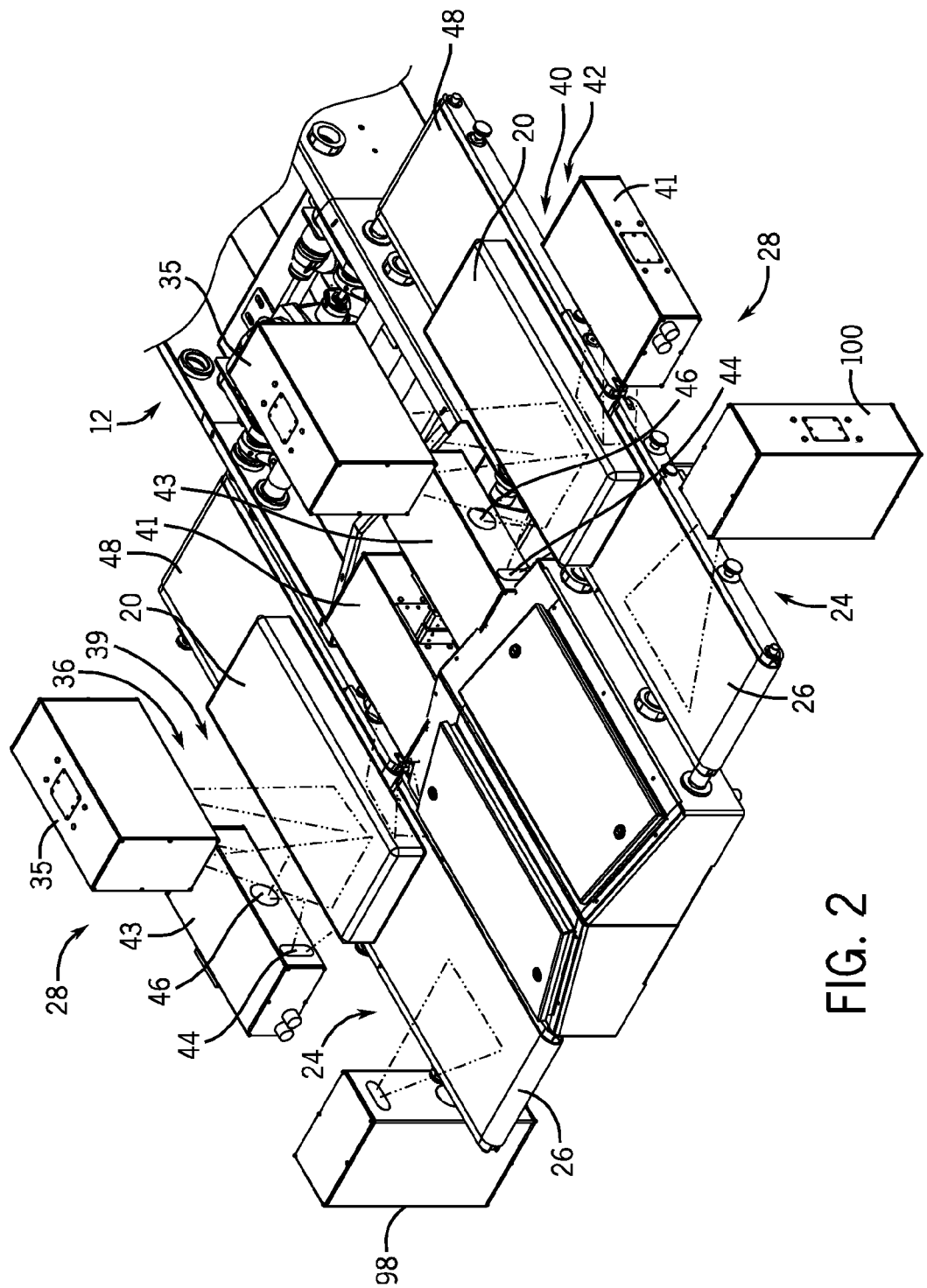
FIG. 2 is a partial, perspective illustration of an exemplary embodiment of two side-by-side systems illustrated in FIG. 1 at a weight station and associated camera vision system.

It should be understood that the cutter conveyor 12 described herein can be duplicated with the system 5 operating side-by-side in parallel as illustrated in FIG. 2. Each cutter conveyor 12 will include a camera vision system 28 and appropriate conveyor, sensor and cutters controlled by a separate PLC 14. It is also envisioned that one PLC can control both cutter conveyors.

The PLC 14 in an exemplary embodiment is coupled to ethernet modules 64, the camera vision system 28 and the cutter conveyor 12. Data relating to the specific type of food product, such as cheese, is stored in a database 16 associated with the PLC 14. A suitable user interface 60 can be used to input, display and output data. Data related to the food product being cut in the system 5 is also stored in a database 32 associated with the camera controller 30 of the camera vision system 28. A suitable user interface 34 coupled to the camera controller 30 can be used to input, display and output data. Data can also be transmitted through various suitable ethernet ports 62 and uplink mechanisms.

Slab Cutter:

A 640 pound block of food product 10, for example cheese, is loaded onto the in-feed conveyor belt of the optimizer food cutter with either a 22 or 28 inch longitudinal dimension depending on the size of the finished cut, for example, if the finished cut is 5.5" long the block will be loaded with the 22" side facing the wire cutter harp 22. If the finished cut length is 7" long the block will be loaded with the 28" side facing the wire cutter harp 22. The block 10 will index into the cut chamber and wait for the lift table to be in position. When the lift table is aligned with the wire cutter harp the block 10 will move forward until it comes in contact with the lift table. The lift table distance from the wire cutter harp 22 determines how thick the block 10 will be cut from the 640 pound block forming a slab 20 of food product. The thickness dimension is the width on the final piece size. The thickness is adjustable by a servo drive and is controlled from a programmable logic controller 14.

Once the block 10 is in position, i.e. indexed, to be cut a plurality of holding cylinders engage to hold the block in position. There are two hold cylinders on each side and one on the top of the block. Once the hold cylinders are in place the wire cutter harp 22 slowly begins moving into the food product (in the illustrated example the food product is a cheese block and will be referred to in this specification as "cheese"), once all the wire is in the cheese it will speed up to cut faster and then before it gets all the way through the cheese block 10 the wire slows down again. Such action prevents wire breakage and product blow out at the bottom of the cheese block 10. The wire cutter harp 22 carriage is servo driven to provide control over the speed of the wire. When the wire gets through the cheese block 10 the tilt table lays the cut slab 20 onto the take away belts and will remain there until the cheese slab is moved to the weigh belt 26. After the cheese slab 20 leaves the discharge belt the cycle starts all over again. The movement and actions are controlled by the PLC 14 based on information in its database 16.

Weigh Belt:

The cheese slab 20 enters the weigh belt 26 from the discharge conveyor, when the cheese slab 20 reaches a photo eye on the weigh belt 26 the belt stops and then the weight of the slab 20 is determined by appropriate scales and transmitted to the PLC 14. The weigh belt 26 is a servo driven belt controlled by the PLC 14.

Scanning Belt and Camera Vision System:

After the cheese slab 20 is weighed and the scanning belt 48 is clear, the cheese slab 20 moves on the scanning belt 48 to be scanned. The weigh belt 26 and scanner belt 48 run at the same speed at this time. There is an encoder on the scanner belt 48 for the vision system 28 to set the appropriate speed of the belt.

A camera vision system 28, including three laser sensors (36, 40, 44), associated camera (39, 42, 46) and a controller 30, for example a computer, will dimensionally scan the slab 20 of cheese to create a volume model which is combined with the weight of the slab 20 to calculate the density to be applied on a slice by slice basis to calculate the optimum cut solution for the slab 20. At a weight station 24 the static weighing belt conveyor 26 measures the weight of the slab which is conveyed under PLC 14 control to the camera vision system 28 along with a bar identification number.

The laser sensors are situated around a gap between the weighing 26 and scanning 48 belt conveyors, triggered by a through beam photocell situated to detect a slab 20 advancing along the conveyors. A rotary shaft encoder attached to the scanning conveyor 48 tracks the advancement of the scanning conveyor 48 and a cheese slab 20 riding on it. The camera vision system 28 scans the cheese slab 20 a predetermined distance, for example every 0.5 mm of conveyor travel, calculates the density of the slab 20, and applies product grading criteria, and calculates the optimum cut solution for the slab 20, and transmits the solution in the form of a cutting list to the PLC 14 for implementation. The optimum cut solution can be transmitted to the PLC 14 directly from the camera vision system controller 30 or through a vision system ethernet switch 38 coupled to the controller 30 and the vision sensors. Upon entering the scanner belt 48 the PLC 14 provides the weight and a unique bar number to identify the slab 20 throughout the process to the camera vision computer 30. The vision computer system 28 detects the presence of the slab 20 using a through beam photocell, and encodes the travel of the slab 20 using a shaft encoder on the scanner belt 48 conveyor.

During scanning the weighing belt conveyor 26 and the scanner belt conveyor 48 are synchronized to travel at the same speed.

The laser sensors project a sheet of laser light in a fan like manner into the scanning region, which is imaged by a camera oriented at an angle to the laser plane. (See FIGS. 1 & 2) For each of the three vision sensors (35, 41, 43) when the laser sheet of light interacts with the slab 20 surface and is reflected back to the camera, the reflected line will move in relation to the distance from the sensor face as the surface moves within the scan zone of the sensor. Using the triangular arrangement between the laser plane and the camera the distance to each reflected point on a surface can be calculated to generate a range profile for the segment of the surface within the camera's unobstructed field of view. By arranging three vision sensors (35, 41, 43) to image the top and side faces of the slab, three range profile segments representing the perimeter of the slab surface can be acquired. The three range profile segments are combined to create a unified 3D slice of the slab 20. Successive image slices are combined as the slab (20 travels through the camera vision system 28 to create a full 3 dimensional model of the slab 20.

The laser planes of each scanner sensor (35, 41, 43) are aligned in a coplanar fashion with each of the other scanner sensors on the line. The cheese slab 20 therefore travels through a curtain of laser light which is viewed by the sensor cameras (39, 42, 46) at calibrated angles to the laser plane, providing a triangulated image of the laser plane where it impinges the slab 20 surface. Three sensors are located around the cheese bar located above, and to each side of the slab, resulting in differential profiling of the opposing slab 20 surfaces. Successive range scans are acquired at predetermined intervals, for example, every 20 thousandths of an inch of slab 20 travel through the camera vision system 28, resulting in a 3 dimensional model of the slab 20.

The gross density of each slab 20 is calculated using the measured weight and calculated volume of the 3D slab model. A density profile can be defined and applied to compensate for density variation between leading and trailing end of the slab 20, representing the top and bottom of the original block 10 respectively. The optimizer food cutter system 5 can provide for up to X equally spaced zones along the length of the slab 20, with each zone having a density adjustment factor represented as a percentage of gross density. The density used to evaluate the slab 20 in the optimization process will therefore be the product of the gross density of the slab and the density adjustment factor for the zone in which the evaluation occurs. Different density adjustment profiles are defined by the number of zones within the profile, with the values for each profile entered through a user interface (60, 34) coupled to each of the PLC 14 and the camera vision controller 30. For any given profile the average of the density adjustment factors must be exactly 100%.

Gross defects not permitted in finished pieces include test coring holes, and major surface voids defined by area and depth. The leading edge of each slab 20 travelling through the camera vision system 28 will be the most uneven surface, which was the top surface of the food product block 10 before cutting it into slabs. Optimization involves maximizing the number of individual pieces of food product 108 cut from the slab 20 that meet a target piece weight and that are within defined size and defect restrictions. The optimizer food cutter evaluates each scan slice of the slab and determines whether or not it is within these restrictions.

The leading edge of the slab 20 as presented through the camera vision system 28 is considered waste which will be used in another product for example, shredded cheese. Typically the trailing end of each slab 20 should have the best surface and represent a good piece.

Each slab 20 may be segmented into one or more density zones for which a density adjustment factor may be applied. The density adjustment factors are selected by profile and entered in the camera vision computer 30 by a user interface 34. The manual input of zone values will be validated to ensure the density adjustment factors applied to the overall slab 20 will result in the correct calculations of aggregate density and weight. In other words, verification checks that the product of the adjusted densities and the volume they apply to equate to the slab weight based on the scanned 3D model dimensions.

The optimizer food cutter system 5 applies the adjusted density to the volumetric profile of the slab 20 starting at the trailing end of the slab 20 to find the greatest number of individual 108 pieces that fit within the slab 20 and meet the weight and size requirements for the product/grade. The product/grade requirements are entered into the camera vision controller 30 and stored in a data base 32. Any sections of the slab 20 that contain defects such as holes exceeding width and area limits will be identified as off-grade, and indicated in the cut table of the database 32 with a grade indicator. Likewise any sections that would result in a piece exceeding the envelope restrictions would be similarly marked.

Four weight values are used to control the process which can be found in the Product/Grade Table stored in the PLC 14 and/or the camera vision system 28 controller 30. These are the Nominal Weight, Target Weight, Upper Limit Weight, and Lower Limit Weight (Nominal Weight—Under Government Allowance weight (UGA)). Four size restriction variables are used to define the allowable size envelope for the product, namely: the Minimum and Maximum Length Limits, Width Limits, and Thickness Limits.

The camera vision controller 30 determines:
1) As many gross defect free Target Weight pieces into the slab model that fit within the size envelope as possible. The only defects that are not permitted are sampling holes and cross sections that are outside the permitted dimensional envelope.
2) To try reducing the target weight to gain an additional piece from the slab. The target weight would be limited to no less than the nominal weight for the food product.
3) If an additional piece can be cut from the slab remnant at a weight between the Target Weight and the Lower Limit Weight, then the camera vision controller 30 will fit the one UGA piece into the cutting decision.
4) The Good waste is balanced around defect or end trim cuts to avoid losing good pieces that are adjacent to defect pieces due to system cutting accuracy.

For purposes of this specification the following definitions apply:

Nominal Weight is the weight that the food product will be sold as, what is printed on the package.

Target Weight is the weight that is targeted to ensure statistically that 99.9% of the food product meet or exceed the Nominal Weight.

Upper Limit Weight is used by the PLC 14 to reject pieces that exceed a predetermined maximum weight.

Lower Limit Weight is the minimum weight that will be allowed for the product/grade, and is defined by the Under Government Allowance (UGA), that establishes how many pieces can be under weight for a given average product weight. For example, in relation to the nominal weight for a 540 g product, the UGA allowance is 25 g, which means one piece per slab could be 515 g.

The last cut on a slab 20 should result in a good piece unless there are gross defects. This means that in a defect free slab 20 only the leading end is trimmed and sent to the trim reject bin, while all of the other pieces 108 result in "on weight" defect free product.

For purposes of this specification, "On Weight" is defined as any piece greater than the package weight minus the UGA allowance for the product, which is represented by the allowable weight range defined in the product grade.

Optimization results in individual bars 108 of food product of substantially equal weight, with the most "on weight" pieces within the size envelope restrictions that may have allowable defect, but are gross defect free.

In an exemplary embodiment of the system 5, an optimized cut solution is a cutting list that can be up to 45 pieces that is communicated from the camera vision controller 30 to the PLC 14, which includes the slab id number, the total slab volume, the calculated slab density, and the number of cuts in the decision. Each cutting/piece index includes the piece sequence number, the calculated cutting index for the trailing edge of the piece (cut location relative to the leading edge of the slab), the grade of the piece as defined in the grade table, the density used in calculating the piece weight, and the calculated weight of the piece.

The PLC 14 implements the cutting of all of the pieces from the slab 20.

The user interface and display 34 includes the density profile along the length of the slab by pseudo color gradient, with density zone limits overlaid, and adjusted densities used in the decision displayed in the same pseudo color gradient along with actual density numbers. The actual density profile of the slab will be displayed using a color palette on the 3D slab model. The display is on a screen associated with the PLC 14 and the camera vision system 28 controller 30. The display may be integral with each controller or remote from either controller.

The camera vision controller 30 includes a decision log stored in the database 32 which includes the scan data, the compressed scan model, the product definition, the cutting decision, and the check weights by slab identification number. In a preferred embodiment the database 32 is configured to save data of the last 1,000 slabs on a revolving basis, which may be retrieved and re-run with different product and grade definitions for future use. The database is SQL based and can be accessed/queried by a plant information system(s).

Once the slab 20 of food product is through the camera planes it travels to the photo eye at the end of the scanner belt 48 where the trim cutter 52, for example an ultrasonic guillotine blade, is mounted. The information including the optimized cut solution of the cheese slab 20 is transferred to the PLC 14 where it controls the scanner belt 48 to index to a position for the trim cut to be taken. When the cheese slab 20 gets into position the trip cutter 52 will make a cut to take the trim off the leading edge of the slab 20. The cheese slab 20 moves to the staging belt 70.

In one embodiment the weight station 24 also includes one of an x-ray machine 98 and an ultrasound machine 100 positioned to scan the cheese slab 20 to profile the density of each slab 20 of food product. The density data is transmitted to the camera vision system 28 controller 30 for use in determining the optimized cut solution for a particular slab 20. The x-ray or ultrasound scan can also identify foreign objects within the slab 20 to avoid equipment damage and related quality problems.

It should be understood that the data transfer for the various sensors, photocells, servo-motors, cutters (18, 22, 58, 78), conveyors and belts (12, 26, 48, 56, 72, 74, 80, 82, 88, 90, 92, 94, 102, 104), camera vision sensors (35, 41, 43), computer 30 and PLC 14 can be by any suitable and reliable means, for example by hard-wire connection, Ethernet transmission, wireless RF or microwave transmission or by optical communication as determined by a manufacturer or user of the system 5.

Staging Belt:

The staging belt 72 is a belt that the slab 20 of food product can be staged on if the next belt in the system 5 is occupied so the scanner belt 48 can scan another block. When the next belt is empty the staging belt 72 starts to discharge the cheese slab 20 to a slitter belt 56.

Slitter Belt 56:

The slitter belts 56 [top (not shown) and bottom] will force the slab 20 of cheese through a series of wire cutters 58. The camera vision system 28 transmits the optimized cut solution to the PLC 14 which will position (index) the particular slab 20 for the slitter wires 58 to obtain the best optimized cut. Once the slitter wires 58 are in position the slab 20 will travel through the wires to be cut into elongated bars 68 and discharge onto the slitter discharge belt where there is a photo eye at the end of the belt. The slitter belt 56 (top and bottom) are servo controlled to control the speed of the slab 20 going through the slitter wires.

Slitter Wires:

The slitter wires 58 are servo controlled as directed by the PLC 14 based on the optimized cut solution so the wires can move to the correct horizontal position relative to the product flow where the slab 20 will be optimized. The position results from instructions from the PLC 14 based on the data obtained and calculated by the camera vision controller 30 and transmitted to the PLC 14 when the slab 20 was scanned by the camera vision system 28. The optimized cut solution was sent to the PLC 14 to be stored in its database 16 until needed for that slab 20.

Guillotine Staging Belt 72:

This belt will stage the elongated cheese bars 68 prior to the indexing belt 74; if the indexing belt 74 is empty, the product will go through the staging belt 72 onto the indexing belt 74. There are a set of photo eye sensors on the indexing belt 74 at the end to stop the indexing belt 74 when the product passes. These elongated bars 68 will then wait until the next set of bars 68 are slit and go onto the staging belt 72. The bars will then stop at the end of the staging belt 72. At this point there is a small gap in-between the sets of bars 68. Since indexing and staging belts 72 are both servo driven belts and the space between the photo eyes is known the staging belt 72 operates to close the gap between the bars 68. Once the gap is closed the staging belt 72 runs at the same speed as the indexing belt 74. The operation of the belts is controlled by the PLC 14. This gap closure is done to help support the back of the front set of bars 68 when they are being cut.

Indexing Belt 74:

The indexing belt 74 is the belt that receives all the information from the camera vision system 28 to index the slab 20 of food product now in elongated bars 68 to be cut into exact weight pieces 108. Once the gap closure is completed the bars 68 together will travel to a second cutter 78, for example an ultrasonic guillotine blade, and make the first index corresponding to the optimized cut solution. When the index position is complete the servo controlled guillotine blade 78 will move down with the ultrasonic system on and cut the cheese into its final dimension. It should be understood that any appropriate cutter system can be used.

Hold Down Belt:

A hold down belt (not shown for figure clarity) is located above the bars of food product 68 on the indexing belt 74. The purpose of this belt is to hold the food product in position while being cut especially on the last cuts of the bars 68. This belt indexes and moves in unison with the indexing belt 74. Both belts are controlled by the PLC 14.

Transport Belt:

A transport conveyor belt 80 is manually adjustable vertically so it can be adjusted depending on the size of the final cut, and it then transfers the cut food product 108 to the pivot conveyor 82. This conveyor belt is run with a variable frequency drive controlled by the PLC 14.

Pivot Conveyor 82:

The transport conveyor 80 transfers the cut food product 108 to the 90 degree conveyor 82. It has a linear actuator coupled to it to pivot the conveyor 82 to an upper and a lower tier (84, 86) 90 degree conveyor. The actuator is servo controlled and the belt is run with a variable frequency drive both controlled by the PLC 14.

Side Shuttle Belt:

A side shuttle belt is configured to assist the bar of food product 108 to move to the 90 degree conveyor 82 and to keep the food product orientation correct. At this point there are two levels to get the product into two lanes for the discharge of the machine. These belts are run with a variable frequency drive controlled by the PLC 14.

90 Degree Conveyors:

These conveyors an upper and lower are transfer conveyors to get the product oriented in the correct direction. These belts are run with a variable frequency drive controlled by the PLC 14.

Speed Up Belt:

Several belts operate to position the product 108, with a gap in between, so they can get weighed on a second scale belt 90. The scale belt 90 requires a larger gap between the products; this belt runs faster than the speed up belt previous and is run with a variable frequency drive controlled by the PLC 14.

Scale System:

After the speed up belt there is a scale belt system 88 that will consist of an in feed belt, the scale belt 90, and an out feed belt. The scale will weigh the individual pieces 108 and if there is an out of range weight it will be rejected at a reject belt 92.

Reject Belt 92:

A reject belt 92 is for rejecting the off weight pieces and transfer product to the accumulation belt 94. The reject belt 92 is associated with an over/under weight bypass conveyor 104. The reject pieces are used for other products such as shredded cheese.

Accumulation Belt:

An accumulation conveyor 94 will accumulate product 108 back to back. This is necessary to adjust product flow for the wrapper process at the packaging station 96. A metering conveyor belt 106 can be used to further regulate the spacing of individual bars 108.

For purposes of this disclosure, the term "coupled" means the joining of two components (electrical or mechanical) directly or indirectly to one another. Such joining may be stationary in nature or moveable in nature. Such joining may be achieved with the two components (electrical or mechanical) and any additional intermediate members being integrally formed as a single unitary body with one another or the two components and any additional member being attached to one another. Such adjoining may be permanent in nature or alternatively be removable or releasable in nature.

It may therefore be appreciated from the above detailed description of the exemplary embodiments of the present disclosure that it maximizes the yield from a specific slab of food product to result in less than 10% of waste and not more than ½% of giveaway over a specific target weight of food product, resulting in the maximum number of individual bars of food product of substantially equal weight from the original block of food product. It is of construction which is both durable and long lasting, and it also requires little or no maintenance to be provided by the user throughout its operating lifetime. It is also be of inexpensive construction to thereby afford it the broadest possible market. Finally, all of the aforesaid advantages and objectives are achieved without incurring any substantial relative disadvantage.

Although the foregoing description of the present exact weight cutting system has been shown and described with reference to particular embodiments and applications thereof, it has been presented for purposes of illustration and description and is not intended to be exhaustive or to limit the invention to the particular embodiments and applications disclosed. It will be apparent to those having ordinary skill in the art that a number of changes, modifications, variations, or alterations to the exact weight cutting system as described herein may be made, none of which depart from the spirit or scope of the present disclosure. The particular embodiments and applications were chosen and described to provide the best illustration of the principles of the cutting system and its practical application to thereby enable one of ordinary skill in the art to utilize the disclosure in various embodiments and with various modifications as are suited to the particular use contemplated. All such changes, modifications, variations, and alterations should therefore be seen as being within the scope of the present disclosure as determined by the appended claims when interpreted in accordance with the breadth to which they are fairly, legally, and equitably entitled.

What is claimed is:

1. A system for cutting blocks of food product into individual bars of substantially equal weight, the system comprising:
    a cutter conveyor configured to receive incoming blocks of food product and move the blocks along a continuum, in-line processing path for cutting;
    a programmable logic controller coupled to the cutter conveyor; and
    a plurality of stations associated with the cutter conveyor with each station coupled to the programmable logic controller, the stations comprising:
        a) a slab cutter station configured to cut a slab portion from a block of food product;
        b) a weight station configured to weigh the slab portion;
        c) a camera vision system configured to create a 3D image of the slab portion, the camera vision system including a camera controller coupled to the camera vision system and to the programmable logic controller, the camera vision system being configured to determine an optimized cut solution of the slab portion from the 3D image and from select data characterizing the food product being cut, the camera vision system being configured to provide the cut solution to the programmable logic controller;
        d) a trim cutter station configured to square the leading edge of the slab portion;
        e) a slit cutter station configured to cut the slab portion into a plurality of elongated bars of substantially equal weight;
        f) an index station configured to position the plurality of bars; and
        g) a width portion cutter station configured to simultaneously, traversely cut the plurality of elongated bars into individual bars of substantially equal weight;
    wherein the programmable logic controller is configured to control the cutting of the food product into individual bars of substantially equal weight.

2. The system for cutting blocks of food product into individual bars of substantially equal weight of claim 1 further comprising:
    a transport conveyor coupled to the cutter conveyor, the transport conveyor configured to reorientate the individual bars 90 degrees and separate each individual bar, the transport conveyor including an upper tier and a lower tier with each tier configured to receive and move the individual bars;
    a weight belt conveyor, coupled to the transport conveyor, configured to weigh each individual bar and reject any individual bar that is either over or under a specified weight as determined by the programmable logic controller; and
    an accumulation conveyor coupled to the weight belt conveyor and configured to move the individual bars of substantially equal weight to a packaging station.

3. The system for cutting blocks of food product into individual bars of substantially equal weight of claim 1 further comprising one of an X-ray machine and an ultrasound machine, coupled to the programmable logic controller, configured to detect foreign body objects in the slab portion and verify a predetermined density value of the slab portion.

4. The system for cutting blocks of food product into individual bars of substantially equal weight of claim 1 wherein the camera vision system includes an array of at least three cameras.

5. The system for cutting blocks of food product into individual bars of substantially equal weight of claim 1 wherein the slab cutter station and the slit cutter station each include a wire cutter device.

6. The system for cutting blocks of food product into individual bars of substantially equal weight of claim 1 wherein the trim cutter and width portion cutter station each include an ultrasonic guillotine blade device.

7. The system for cutting blocks of food product into individual bars of substantially equal weight of claim 1 including a trim removal conveyor coupled to the trim cutter station.

8. The system for cutting blocks of food product into individual bars of substantially equal weight of claim 2 including an over/under weight bypass conveyor coupled to the weight belt conveyor.

9. The system for cutting blocks of food product into individual bars of substantially equal weight of claim 2 including a metering belt, coupled to the accumulation conveyor, configured to control the flow of individual bars of food product to the packaging station.

10. The system for cutting blocks of food product into individual bars of substantially equal weight of claim 1 wherein the food product is cheese.

11. A system for cutting blocks of food product into individual bars of substantially equal weight, the system comprising:
    a cutter conveyor configured to receive incoming blocks of food product and move the blocks along a continuum, in-line processing path for cutting;
    a programmable logic controller coupled to the cutter conveyor;
    a plurality of stations associated with the cutter conveyor with each station coupled to the programmable logic controller, the stations comprising:
        a) a slab cutter station configured to cut a slab portion from a block of food product;
        b) a weight station configured to weigh the slab portion;

c) a camera vision system configured to create a 3D image of the slab portion, the camera vision system including a camera controller coupled to the camera vision system and to the programmable logic controller, the camera vision system being configured to determine an optimized cut solution of the slab portion from the 3D image and from select data related to the food product being cut, the camera vision system being configured to provide the cut solution to the programmable logic controller;

d) a trim cutter station configured to square the leading edge of the slab portion;

e) a slit cutter station configured to cut the slab portion into a plurality of elongated bars of substantially equal weight;

f) an index station configured to position the plurality of bars; and g) a width portion cutter station configured to simultaneously, traversely cut the plurality of elongated bars into individual bars of substantially equal weight;

a transport conveyor coupled to the cutter conveyor, the transport conveyor configured to reorientate the individual bars 90 degrees and separate each individual bar, the transport conveyor including an upper tier and a lower tier with each tier configured to receive and move the individual bars;

a weight belt conveyor, coupled to the transport conveyor, configured to weigh each individual bar and reject any individual bar that is either over or under a specified weight as determined by the programmable logic controller; and an accumulation conveyor coupled to the weight belt conveyor and configured to move the individual bars of substantially equal weight to a packaging station.

12. The system for cutting blocks of food product into individual bars of substantially equal weight of claim 11 further comprising one of an X-ray machine and an ultrasound machine, coupled to the programmable logic controller, configured to detect foreign body objects in the slab portion and verify a predetermined density value of the slab portion.

13. The system for cutting blocks of food product into individual bars of substantially equal weight of claim 11 wherein the camera vision system includes an array of at least three cameras.

14. The system for cutting blocks of food product into individual bars of substantially equal weight of claim 11 wherein the slab cutter station and the slit cutter station each include a wire cutter device and wherein the trim cutter and width portion cutter station each include an ultrasonic guillotine blade device.

15. The system for cutting blocks of food product into individual bars of substantially equal weight of claim 11 wherein the food product is cheese.

* * * * *

UNITED STATES PATENT AND TRADEMARK OFFICE
CERTIFICATE OF CORRECTION

PATENT NO. : 8,375,833 B2
APPLICATION NO. : 13/547576
DATED : February 19, 2013
INVENTOR(S) : Schmidt It is certified that error appears in the above-identified patent and that said Letters Patent is hereby corrected as shown below:

In the title page:
Item (75) Inventor:
"Richard J. Schmidt, Fond du Lac, WI (US)" should read --Richard F. Schmidt, Fond du Lac, WI (US)--.

Signed and Sealed this
Twenty-third Day of April, 2013

Teresa Stanek Rea
*Acting Director of the United States Patent and Trademark Office*